United States Patent [19]

Engel

[11] 4,183,942

[45] Jan. 15, 1980

[54] INSECTICIDAL (β-PHENYL-β-SUBSTITUTED-VINYL)CYCLOPROPANECARBOXYLATES

[75] Inventor: John F. Engel, Medina, N.Y.

[73] Assignee: FMC Corporation, Philadelphia, Pa.

[21] Appl. No.: 954,036

[22] Filed: Oct. 23, 1978

Related U.S. Application Data

[63] Continuation-in-part of Ser. No. 718,252, Aug. 27, 1976, abandoned.

[51] Int. Cl.$^2$ .................. A01N 9/24; C07C 121/60; C07C 69/76
[52] U.S. Cl. .................. 424/274; 260/465 D; 560/8; 560/18; 560/21; 560/36; 560/45; 560/47; 560/57; 560/59; 560/65; 560/101; 560/102; 542/429; 542/430; 424/282; 424/285; 424/304; 424/308; 424/309
[58] Field of Search ................ 542/430, 429; 260/465 D; 560/8, 101, 102, 21, 57, 59, 65, 18, 36, 45, 47; 424/304, 308, 309, 274, 285, 282

[56] References Cited

U.S. PATENT DOCUMENTS

| | | | |
|---|---|---|---|
| 3,723,469 | 3/1973 | Martel | 560/8 |
| 3,786,052 | 1/1974 | Martel et al. | 560/8 |
| 4,024,163 | 5/1977 | Elliott et al. | 560/8 |

FOREIGN PATENT DOCUMENTS 851465  8/1977  Belgium .

Primary Examiner—Jane S. Myers
Attorney, Agent, or Firm—Robert M. Kennedy; H. R. Ertelt

[57] ABSTRACT

New insecticidal (β-phenyl-β-substituted-vinyl)cyclopropanecarboxylates in which the β-substituent may be halogen or lower haloalkyl are described and their preparation and insecticidal utility are exemplified.

10 Claims, No Drawings

INSECTICIDAL (β-PHENYL-β-SUBSTITUTED-VINYL)CYCLOPROPANECARBOXYLATES

This is a continuation-in-part of copending application Ser. No. 718,252 filed Aug. 27, 1976, now abandoned.

This invention relates to the general field of insecticides, particularly to insecticides for use in agriculture to protect crops and animals, but also for household and insecticidal use. The active compounds of this invention are insecticidal esters of 2,2-dimethyl-3-(β-phenyl-β-substituted-vinyl)cyclopropanecarboxylic acid.

Ever since the structures of naturally occurring pyrethroids were elucidated, synthesis efforts have been directed toward the preparation of related compounds of enhanced insecticidal activity and improved stability toward air and light. A noteworthy advance in this area was the discovery by Elliott et al of certain highly active compounds remarkably resistant to photooxidative degradation, for example, 3-phenoxybenzyl 3-(β,β-dichlorovinyl)-2,2-dimethylcyclopropanecarboxylate, Nature, 246, 169 (1973), Belgian Pat. Nos. 800,006 and 818,811.

Despite the extensive activity in the field of insecticidal cyclopropanecarboxylates, insecticidal 2,2-dimethyl-3-(β-phenyl-β-substituted-vinyl)cyclopropanecarboxylates have not been described prior to the present invention.

The compounds of the present invention have the formula:

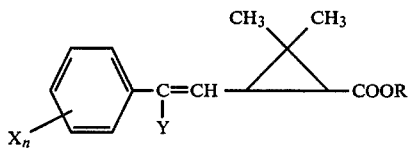

in which X is halogen, such as fluoro, chloro, or bromo, cyano, nitro, aryl, such as phenyl, thienyl, furyl, or pyridyl, aralkyl, such as benzyl, lower alkyl, lower haloalkyl, lower alkoxy, lower alkylthio, aryloxy, arylthio, di-(lower alkyl) amino, or methylenedioxy; Y is halogen, for example chloro, bromo, or fluoro, preferably chloro or lower haloalkyl; n is 0, 1, 2, or 3, more commonly 0, 1, or 2; and R is the residue of an alcohol which in combination with an appropriate acid moiety yields an insecticidal cyclopropanecarboxylate. A wide range of such alcohols are known to the insecticide art. Those R groups useful in compounds of the present invention include:

(1) a benzyl- or phenoxy-substituted benzyl group of the formula:

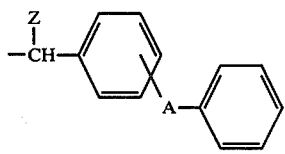

wherein Z is hydrogen, methyl, cyano, ethynyl, or phenyl, and A is —O— or —CH₂—;

(2) a benzyl- or phenoxy-substituted furylmethyl group such as 5-benzyl-3-furylmethyl;

(3) an imidomethyl group such as maleimidomethyl, phthalimidomethyl, and tetrahydrophthalimidomethyl;

(4) a benzyl group substituted in at least two ring positions with chloro, methyl, or methylenedioxy groups, for example 3,4-methylenedioxybenzyl, 2-chloro-4,5-methylenedioxybenzyl, and 2,4-dimethylbenzyl;

(5) a substituted cyclopentenonyl group such as allethrolonyl.

The more readily available R groups which give active insecticides of the present invention are 3-phenoxybenzyl, α-cyano-3-phenoxybenzyl, and 5-benzyl-3-furylmethyl.

In the substituents X and Y, lower means having one to four carbon atoms, preferably, and particularly for the haloalkyl and amino substituents, having one or two carbon atoms. Examples of halomethyl substituents include trichloromethyl and trifluoromethyl groups.

The preparation and insecticidal properties of the compounds of this invention are illustrated in the following specific examples. Unless otherwise specified, all temperatures are in degrees centigrade, and concentration of liquid volume was carried out under the reduced pressure produced by a water aspirator.

EXAMPLE 1

Synthesis of 3-(β-Chloro-β-phenylvinyl)-2,2-dimethylcyclopropanecarbonyl Chloride A. Preparation of Ethyl 3-(β-chloro-β-phenylvinyl)-2,2-dimethylcyclopropanecarboxylate To a solution of 28.35 g of diethyl benzylphosphonate in tetrahydrofuran at −78° was added one equivalent of n-butyllithium in hexane. After the reaction mixture was stirred at −70° for 40 minutes, 124 ml of carbon tetrachloride was added. The mixture was stirred for an additional 40 minutes at −70°, then 23.6 g of caronaldehyde was added. The mixture was allowed to warm to room temperature, and 27 ml of water was then added. The reaction mixture was extracted with diethyl ether. The ethereal extract was concentrated, treated with 200 ml of pentane at −50°, triturated, and the pentane decanted. The residue was treated with 200 ml of pentane at −30°, triturated, and the pentane decanted. The combined decantates were concentrated to an oil, which was treated with 19 g of sodium bisulfite in 50 ml of water. The mixture was extracted with 50 ml of diethyl ether. The extract was washed with 50 ml of saturated aqueous sodium chloride solution, dried over anhydrous magnesium sulfate, and concentrated to yield 19.71 g of oil. The oil was purified by chromatography on 98.5 g of silica gel, with 95:5 hexane:ether as eluent. The solvents were removed under reduced pressure to yield 14.4 g of ethyl 3-(β-chloro-β-phenylvinyl)-2,2-dimethylcyclopropanecarboxylate as a mixture of isomers containing cis, trans, (E), and (Z) forms. The nmr and ir spectra were consistent with the assigned structure.

B. Preparation of 3-(β-chloro-β-phenylvinyl)-2,2-dimethylcycloproanecarboxylic acid A mixture of 16.91 g of ethyl 3-(β-chloro-β-phenylvinyl)-2,2-dimethylcyclopropanecarboxylate, 2.57 g of sodium hydroxide, 4.6 ml of water, and 72 ml of ethanol was heated at 55° for 17 hours. The mixture was allowed to cool and was concentrated to near dryness. A saturated aqueous sodium chloride solution was added to the concentrate and the mixture thus formed was washed with chloroform. The aqueous phase was acidified with 3% hydrochloric acid and extracted with diethyl ether. The ethereal extract was concentrated to yield approximately 14.57 g of 3-($\beta$-chloro-$\beta$-phenylvinyl)-2,2-dimethylcyclopropanecarboxylic acid. The nmr and ir spectra were consistent with the assigned structure.

C. Preparation of 3-($\beta$-chloro-$\beta$-phenylvinyl)-2,2-dimethylcyclopropanecarbonyl chloride A 14.57 g portion of 3-($\beta$-chloro-$\beta$-phenylvinyl)-2,2-dimethylcyclopropanecarboxylic acid was dried by twice azeotropically distilling the contained water with benzene. The acid was then diluted with 52 ml of benzene, and 9 ml of thionyl chloride was added to the solution. The mixture was heated under reflux for 3 hours. The excess thionyl chloride was removed by distillation. More benzene was added, and further distillation removed all traces of thionyl chloride. The reaction mixture was diluted to a volume of 100 ml with benzene. One third of this solution was used for the preparation of each of three esters described below.

EXAMPLE 2

Synthesis of 3-phenoxybenzyl 3-($\beta$-chloro-$\beta$-phenylvinyl)-2,2-dimethylcyclopropanecarboxylate A 33.3 ml portion of the 3-($\beta$-chloro-$\beta$-phenylvinyl)-2,2-dimethylcyclopropanecarbonyl chloride solution in benzene of Example 1C was added at 0° C. to a stirred solution of 4.0 g of 3-phenoxybenzyl alcohol and 4 ml of pyridine in 26 ml of benzene. The reaction mixture was stirred at ambient temperature for 14 hours. The pyridine hydrochloride was removed by filtration. The filtrate was evaporated under reduced pressure to give 8.6 g of residual oil. The residual oil was purified on a chromatographic column of 42.5 g silica gel. Elution was accomplished with 860 ml of 20% methylene chloride/80% pentane to give 6.41 g (77%) of 3-phenoxybenzyl 3-($\beta$-chloro-$\beta$-phenylvinyl)-2,2-dimethylcyclopropanecarboxylate.

Analysis: Calc'd for $C_{27}H_{25}ClO_3$: C, 74.90; H, 5.82; Found: C, 74.81; H, 5.83.

EXAMPLE 3

Synthesis of 5-benzyl-3-furylmethyl 3-($\beta$-chloro-$\beta$-phenylvinyl)-2,2-dimethylcyclopropanecarboxylate This compound was prepared by the method of Example 2, with 33.3 ml of the 3-$\beta$-chloro-$\beta$-phenylvinyl)-2,2-dimethylcyclopropanecarbonyl chloride/benzene solution, 3.75 g of 5-benzyl-3-furylmethyl alcohol and 4 ml of pyridine in 26 ml of benzene. The yield was 6.14 g (46%) of 5-benzyl-3-furylmethyl 3-($\beta$-chloro-$\beta$-phenylvinyl)-2,2-dimethylcyclopropanecarboxylate.

Analysis: Calc'd for $C_{26}H_{25}ClO_3$: C, 74.19; H, 5.99; Found: C, 74.10; H, 6.03.

EXAMPLE 4

Synthesis of $\alpha$-cyano-3-phenoxybenzyl 3-($\beta$-chloro-$\beta$-phenylvinyl)-2,2-dimethylcyclopropanecarboxylate This compound was prepared by the method of Example 2, with 33.3 ml of the 3-($\beta$-chloro-$\beta$-phenylvinyl)-2,2-dimethylcyclopropanecarbonyl chloride/benzene solution, 4.50 g of $\alpha$-cyano-3-phenoxybenzyl alcohol and 4 ml of pyridine in 26 ml of benzene. The yield was 7.12 g (81%) of $\alpha$-cyano-3-phenoxybenzyl 3-($\beta$-chloro-$\beta$-phenylvinyl)-2,2-dimethylcyclopropanecarboxylate.

Analysis: Calc'd for $C_{28}H_{24}ClNO_3$: C, 73.43; H, 5.28; N, 3.06; Found: C, 73.60; H, 5.31; N, 3.08.

EXAMPLE 5

Toxicity to Insects and Mites

Initial Contact Activity

One quarter gram of test compound was dissolved in 20 ml of acetone and this solution was dispersed in 180 ml of water containing one drop of isooctylphenyl polyethoxyethanol. Aliquots of this solution, which corresponds to 1250 ppm of active ingredient, were diluted with an appropriate amount of water to provide solutions containing the reported concentration of active ingredient. Test organisms and techniques were as follows: the activities against the Mexican bean beetle (*Epilachna varivestis* Muls.) and the southern armyworm (*Spodoptera eridania* [Cram.]) were evaluated by dipping the leaves of pinto bean plants into the test solution and infesting the leaves with the appropriate immature-form insects when the foliage had dried; the activity against the pea aphid (*Acyrthosiphon pisum* [Harris]) was evaluated on broad bean plants whose leaves were dipped before infestation with adult aphids; the activity against two-spotted spider mites (*Tetranychus urticae* Koch) was evaluated on pinto bean plants whose leaves were dipped after infestation with adult mites; the activity against the milkweed bug (*Oncopeltus fasciatus* [Dallas]) and the boll weevil (*Anthonomus grandis* Boheman) were evaluated by spraying the test solutions into glass dishes or jars containing the adult insects. All organisms in the test were maintained in a holding room at 80° F. and 50% relative humidity for an exposure period of 48 hours. At the end of this time, the dead and living insects or mites were counted, and the percent kill was calculated. Results of these tests are summarized in Table 1.

Residual Contact Activity

The residual contact activity of the compounds was determined on the same organisms using the techniques described above, except that in each case the treated surface was allowed to dry and was exposed to normal light and air for seven days before introduction of the mites or insects. Results of these tests are summarized in Table 2.

EXAMPLE 6

Comparative Tests for Initial Contact Activity

For the purpose of demonstrating relative initial contact insecticidal efficacy, the compounds of Examples 2 and 4 were compared with the allethrolonyl, 3-phenoxybenzyl, and $\alpha$-cyano-3-phenoxybenzyl esters of 3-($\beta,\beta$-diphenylvinyl)-2,2-dimethylcyclopropanecarboxylic acid, referred to in Table 3 as compounds A, B, and C respectively. The compounds were tested in accordance with the procedures set forth in Example 5, *Toxicity to Insects and Mites, Initial Contact Activity.* The data reported in Table 3 show the claimed compounds to be vastly superior in insecticidal and miticidal efficacy to compounds A, B, and C.

It is anticipated that, in the normal use of the compounds of the present invention as insecticides, the compounds will usually not be employed free from admixture or dilution, but will ordinarily be used in a suitable formulated state compatible with the method of application. The insecticidal cyclopropanecarboxylates of this invention may be formulated with the usual additives and extenders used in the preparation of pesticidal compositions. The toxicants of this invention, like most pesticidal agents, are incorporated with the adjuvants and carriers normally employed for facilitating the dispersion of active ingredients, recognizing the accepted fact that the formulation and mode of application of a toxicant may affect the activity of the material. The present compounds may be applied, for example, as a spray, dust, or granule, to the area in which pest control is desired, the choice of application varying of course with the type of pest and the environment. Thus, the compounds of this invention may be formulated as granules of large particle size, as powdery dusts, as wettable powders, as emulsifiable concentrates, as solutions, and the like.

Dusts are admixtures of the active ingredients with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as dispersants and carriers for the toxicant. These finely divided solids have an average particle size of less than about 50 microns. A typical dust formulation useful herein contains 10.0 parts of 3-phenoxybenzyl 3-($\beta$-chloro-$\beta$-phenylvinyl)-2,2-dimethylcyclopropanecarboxylate, 30.0 parts of bentonite clay, and 60.0 parts of talc.

The compounds of the present invention may be made into liquid concentrates by solution or emulsion in suitable liquids, and into solid concentrates by admixtures with talc, clays, and other known solid carriers used in the pesticide art. The concentrates are compositions containing about 5-50% toxicant, and 95-50% inert material which includes dispersing agents, emulsifying agents, and wetting agents. The concentrates are diluted for practical application, with water or other liquid for sprays or with additional solid carrier for use as dusts. Typical carriers for solid concentrates (also called wettable powders) include fuller's earth, kaolin clays, silicas, and other highly absorbent, readily wet inorganic diluents. A solid concentrate formulation useful herein contains 1.5 parts each of sodium lignosulfonate and sodium laurylsulfate as wetting agents, 25.0 parts of 5-benzyl-3-furylmethyl 3-($\beta$-chloro-$\beta$-phenylvinyl)-2,2-dimethylcyclopropanecarboxylate and 72.0 parts of bentonite clay.

Useful liquid concentrates include the emulsifiable concentrates, which are homogeneous liquid or paste compositions readily dispersed in water or other dispersant, and may consist entirely of the toxicant with a liquid or solid emulsifying agent, or may also contain a liquid carrier such as xylene, heavy aromatic naphthas, isophorone and other nonvolatile organic solvents. For application, these concentrates are dispersed in water or other liquid carrier, and normally applied as a spray to the area to be treated.

Typical wetting, dispersing or emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1-15% by weight of the pesticidal composition.

Other useful formulations include simple solutions of the active ingredient in a solvent in which it is completely soluble at the desired concentration, such as acetone or other organic solvents.

The concentration of the toxicant in the dilution generally used for application is normally in the range of about 2% to about 0.001%. Many variations of spraying and dusting compositions in the art may be used, by substituting a compound of this invention into compositions known or apparent to the art.

Pesticidal compositions may be formulated and applied with other active ingredients, including other insecticides, nematicides, acaricides, fungicides, plant growth regulators, fertilizers, etc. In applying the chemicals, it is obvious that an effective amount and concentration of the compound of the invention should be employed. For agricultural application the active ingredient of the invention may be applied at a rate of 75 to 4000 g per hectare, preferably 150 to 3000 g per hectare.

It is apparent that many modifications may be made in the structure, preparation, formulation and application of the compounds of this invention, without departing from the spirit and scope of the invention and of the following claims.

Table 1

| | | Initial Toxicity to Insects and Mites | | | | |
|---|---|---|---|---|---|---|
| Compound | Conc. | | | % Kill | | |
| of Example | (PPM) | BB | AW | PA | M | MWB |
| 2 | 1250 | 100 | 100 | 100 | 97 | 100 |
| | 156 | 100 | 100 | 40 | 3.6 | 20 |
| 3 | 1250 | 100 | 100 | 100 | 44 | 100 |
| | 156 | 100 | 100 | 60 | 8.9 | 80 |
| 4 | 1250 | 100 | 100 | 56 | 100 | 100 |
| | 156 | 100 | 100 | 100 | 4.7 | 90 |

BB: Mexican bean beetle
AW: Southern armyworm
PA: Pea aphid
M: Two-spotted spider mite
MWB: Milkweed bug Table 2

| | | Residual (7-Day) Toxicity to Insects and Mites | | | | | |
|---|---|---|---|---|---|---|---|
| Compound | Conc. | | | % Kill | | | |
| of Example | (PPM) | BB | AW | PA | M | MWB | BW |
| 2 | 1250 | 100 | 100 | 100 | 0 | 10 | 20 |
| | 312 | 100 | 59 | 89 | 0 | 10 | 20 |
| 3 | 1250 | 100 | 25 | 17 | 0 | 5 | 15 |
| | 312 | 75 | 0 | 8 | 0 | 5 | 15 |
| 4 | 1250 | 100 | 100 | 100 | 0 | 80 | 30 |
| | 312 | 100 | 100 | 100 | 0 | 60 | 45 |

BB: Mexican bean beetle
AW: Southern armyworm
PA: Pea aphid
M: Two-spotted spider mite
MWB: Milkweed bug
BW: Boll weevil

Table 3

| Compound | Conc. (PPM) | Comparative Initial Contact Activity % Kill | | | | |
|---|---|---|---|---|---|---|
| | | BB | AW | PA | M | MWB |
| Example 2 | 1250 | 100 | 100 | 100(100) | 97 | 100(100) |
| | 156 | 100 | 100(72) | 40(100) | 3.6 | 20(80) |
| | 78 | — | —(53) | —(100) | — | —(43) |
| | 39 | 100(100) | 42(12) | 0 | 5.1 | 0 |
| | 20 | — | —(65) | — | — | — |
| | 2.5 | 100(100) | 0 | — | — | — |
| Example 4 | 1250 | 100 | 100 | 56 | 100 | 100 |
| | 156 | 100 | 100(100) | 100 | 4.7 | 90(95) |
| | 39 | 95(100) | 100(84) | 100(75) | 5.6 | 10(10) |
| | 10 | 100(62) | 27(0) | —(25) | — | 5 |
| | 2.5 | 89(93) | 17 | — | — | — |
| Compound A | 1250 | 60 | 0 | 7 | 0 | 35 |
| | 312 | 45 | 0 | 0 | 0 | 0 |
| | 78 | 11 | 0 | 0 | 0 | 10 |
| | 20 | 41 | 0 | 0 | 0 | 0 |
| Compound B | 1250 | 94 | 0 | 2 | 0 | 20 |
| | 312 | 19 | 0 | — | 0 | 20 |
| | 78 | 0 | 0 | — | 0 | 5 |
| Compound C | 1250 | 93 | 6 | 0 | 5 | 15 |
| | 312 | 89 | 0 | — | 0 | 25 |
| | 78 | 25 | 0 | — | 0 | 0 |

Mortality figures in parentheses are from a separate test. See Example 6 for identity of compounds A, B and C.

I claim:

1. An insecticidal compound of the formula:

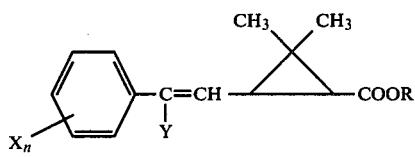

in which X is halogen, cyano, nitro, aryl, aralkyl, aryloxy, arylthio, alkyl of $C_1$–$C_4$, alkoxy of $C_1$–$C_4$, alkylthio of $C_1$–$C_4$, haloalkyl of $C_1$–$C_2$, dialkylamino in which alkyls are $C_1$–$C_2$, or methylenedioxy; Y is halogen or haloalkyl of $C_1$–$C_2$; n is 0, 1, 2, or 3; and R is an alcohol residue selected from the group consisting of:

(a) a benzyl- or phenoxy-substituted benzyl group of the formula:

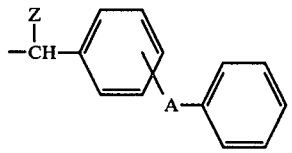

wherein Z is hydrogen, methyl, cyano, ethynyl, or phenyl and A is —O— or —$CH_2$—;

(b) 5-benzyl-3-furylmethyl;

(c) an imidomethyl group selected from the group consisting of maleimidomethyl, phthalimidomethyl, and tetrahydrophthalimidomethyl; and (d) a benzyl group substituted in at least two ring positions with chloro, methyl, or methylenedioxy groups, selected from the group consisting of 3,4-methylenedioxybenzyl, 2-chloro-4,5-methylenedioxybenzyl, and 2,4-dimethylbenzyl.

2. The compound of claim 1 in which X is chloro, cyano, methyl, methoxy, or methylenedioxy; Y is chloro or bromo; and n is 0, 1, or 2.

3. The compound of claim 2 in which Y is chloro and n is 0.

4. The compound of claim 3 in which R is 3-phenoxybenzyl, α-cyano-3-phenoxybenzyl, or 5-benzyl-3-furylmethyl.

5. The compound of claim 4 which is 3-phenoxybenzyl 3-(β-chloro-β-phenylvinyl)-2,2-dimethylcyclopropanecarboxylate.

6. The compound of claim 4 which is 5-benzyl-3-furylmethyl 3-(β-chloro-β-phenylvinyl)-2,2-dimethylcyclopropanecarboxylate.

7. The compound of claim 4 which is α-cyano-3-phenoxybenzyl 3-(β-chloro-β-phenylvinyl)-2,2-dimethylcyclopropanecarboxylate.

8. An insecticidal composition comprising an insecticidally effective amount of a compound of claim 1 in admixture with an agriculturally acceptable extender.

9. An insecticidal composition of claim 8 which contains a surface active agent.

10. A method of controlling insects which comprises applying to the locus where control is desired an insecticidally effective amount of a compound of claim 1.

* * * * *